United States Patent
Van Landuyt

(10) Patent No.: US 7,638,087 B2
(45) Date of Patent: Dec. 29, 2009

(54) MEDICO-SURGICAL TUBES AND METHODS OF MANUFACTURE

(75) Inventor: Christophe Van Landuyt, London (GB)

(73) Assignee: Smiths Group Plc, London (GB)

( * ) Notice: Subject to any disclaimer, the term of this patent is extended or adjusted under 35 U.S.C. 154(b) by 1659 days.

(21) Appl. No.: 10/349,926

(22) Filed: Jan. 24, 2003

(65) Prior Publication Data
US 2003/0109851 A1    Jun. 12, 2003

(51) Int. Cl.
*B28B 1/00*    (2006.01)
(52) U.S. Cl. ........................... 264/655; 604/525
(58) Field of Classification Search ......... 604/523–528, 604/544; 264/655
See application file for complete search history.

(56) References Cited

U.S. PATENT DOCUMENTS

| | | | |
|---|---|---|---|
| 2,966,373 A * | 12/1960 | Yount | ................ 285/213 |
| 5,085,649 A | 2/1992 | Flynn | |
| 5,215,614 A * | 6/1993 | Wijkamp et al. | ........... 156/153 |
| 5,542,937 A * | 8/1996 | Chee et al. | ............... 604/523 |
| 5,699,835 A | 12/1997 | Nakagawa et al. | |
| 5,702,372 A | 12/1997 | Nelson | |
| 5,771,965 A | 6/1998 | Inaba et al. | |
| 6,045,547 A | 4/2000 | Ren et al. | |
| 6,290,666 B1 * | 9/2001 | Devonec | ................ 623/1.16 |

FOREIGN PATENT DOCUMENTS

| | | |
|---|---|---|
| GB | 1427958 | 3/1976 |
| GB | 2043201 | 10/1980 |

* cited by examiner

*Primary Examiner*—Nicholas D Lucchesi
*Assistant Examiner*—Christopher D Koharski
(74) *Attorney, Agent, or Firm*—Connolly Bove Lodge & Hutz LLP

(57) ABSTRACT

An epidural catheter has a closed, soft patient end region with a side opening. The catheter is formed from a two-layer extruded tube in which the outer layer is of a harder material than the inner layer. A heated pin is inserted in one end of the tube to expand its diameter. An annular grinding tool is then moved along the expanded region to remove the outer, hard layer in this region. The end of the tube is subsequently closed and the side opening is formed.

11 Claims, 2 Drawing Sheets

MEDICO-SURGICAL TUBES AND METHODS OF MANUFACTURE

BACKGROUND OF THE INVENTION

This invention relates to medico-surgical tubes and methods of manufacture.

The invention is more particularly concerned with tubes having a soft tip, and with methods of manufacture of such tubes.

It is often desirable for medico-surgical tubes or catheters to have a soft tip, so as to reduce trauma when the tip contacts patient tissue. In epidural catheters, a soft tip reduces the risk that the catheter will damage the dura. Various arrangements have been proposed for providing a soft tip, such as by attaching or moulding a separate component of a softer material onto the shaft of the catheter. Such an arrangement is not entirely satisfactory because a separate assembly operation is needed to form the tip, leading to increased manufacturing expense. Also, there is always some risk that a separate component might become detached from the body of the catheter. Other arrangements in which the rear part of the catheter is reinforced can also be difficult to make by automated assembly, thereby making the catheter relatively expensive.

BRIEF SUMMARY OF THE INVENTION

It is an object of the present invention to provide an improved medico-surgical tube and method of manufacture of a such a tube.

According to one aspect of the present invention there is provided a medico-surgical tube having an inner layer and an outer layer, the outer layer being of a harder material than the inner layer, and a part at least of the outer layer being removed along a region of the tube so as to make the region of the tube softer and more flexible than the remainder of the tube.

The region is preferably at one end of the tube, such as the patient end of the tube. The patient end of the tube is preferably closed and has a side opening in the region. The external diameter of the inner layer is preferably enlarged where the part at least of the outer layer is removed such that the outer diameter of the tube is substantially constant along the tube. The outer layer is preferably removed through its entire thickness and the inner layer is exposed externally along the region. The tube may be an epidural catheter.

According to another aspect of the present invention there is provided a method of making a medico-surgical tube including the steps of providing a tubular member with an inner layer and an outer layer, the outer layer being of a harder material than the inner layer, enlarging the diameter of the tubular member along a region of the tubular member, and removing a part at least of the outer layer along the region to make the region softer and more flexible than the remainder of the tube.

The part at least of the outer layer is preferably removed along the region to a thickness such that the external diameter of the region is substantially equal to that of the remainder of the tube. The outer layer is preferably removed through its entire thickness along the region. The diameter may be enlarged by inserting a heated pin into the tubular member along the region, the diameter of the pin being preferably substantially equal to the external diameter of the tubular member less the thickness of the inner layer. The part at least of the outer layer may be removed by grinding while the pin is in the tubular member. The part at least of the outer layer may be removed by moving an annular grinding tool axially along the region. The method may include the step of smoothing the region after removing the part at least of the outer layer. The region is preferably at one end of the tube, such as at the patient end of the tube. The method may include the step of subsequently end forming the end of the tube closed and forming a side opening in the tube in the region. The tubular member is preferably provided by extruding.

According to a further aspect of the invention there is provided a tube made by the method of the other aspect of the invention.

An epidural catheter and a method of making an epidural catheter according to the present invention, will now be described, by way of example, with reference to the accompanying drawings.

DETAILED DESCRIPTION OF THE PREFERRED EMBODIMENT

Figure 1:
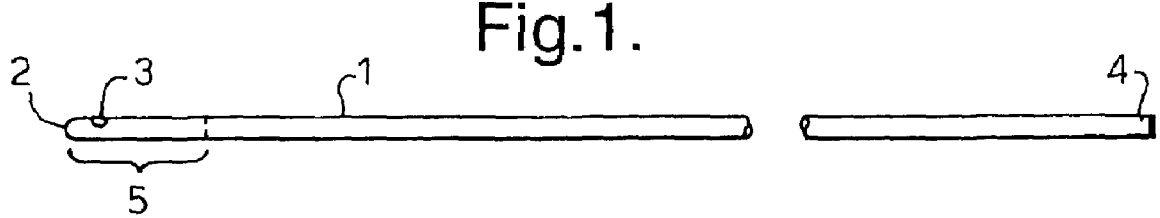
FIG. 1 is a side elevation view of the catheter.

With reference first to FIG. 1, the catheter 1 is about 75-100 cm long with a rounded tip 2 at its patient end and a side opening 3 close to the tip. The machine end 4 of the catheter 1 is open and cut square for attachment to a conventional epidural connector, not shown. A region 5 at the patient end of the catheter 1 is softer than the remainder of the catheter and extends for a distance of about 5 cm.

The way in which the soft region 5 is provided at the tip of the catheter 1 will become apparent from reference to FIGS. 2 to 5 showing steps in manufacture of the catheter.

Figure 2:
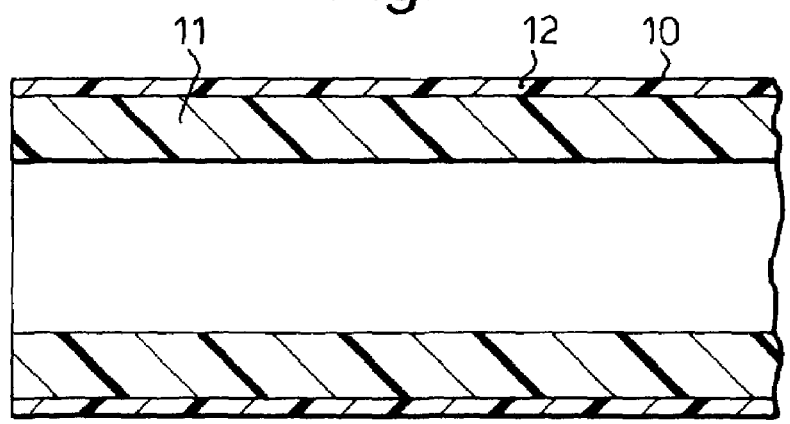
FIGS. 2 to 5 are enlarged cross-sectional side elevation views of the patient end of the catheter at various stages of manufacture.

Turning first to FIG. 2, a length of tubing 10 is provided having an inner layer 11 and an outer layer 12; the outer layer is harder than the inner layer. Both layers 11 and 12 may be of the same polymer, such as PVC, but with differing amounts of plasticizer. Alternatively, the layers could be of different polymers, such as an inner layer of PVC and an outer layer of ABS, nylon or polycarbonate. The tubing 10 is extruded but could be formed in any conventional way.

Figure 3:
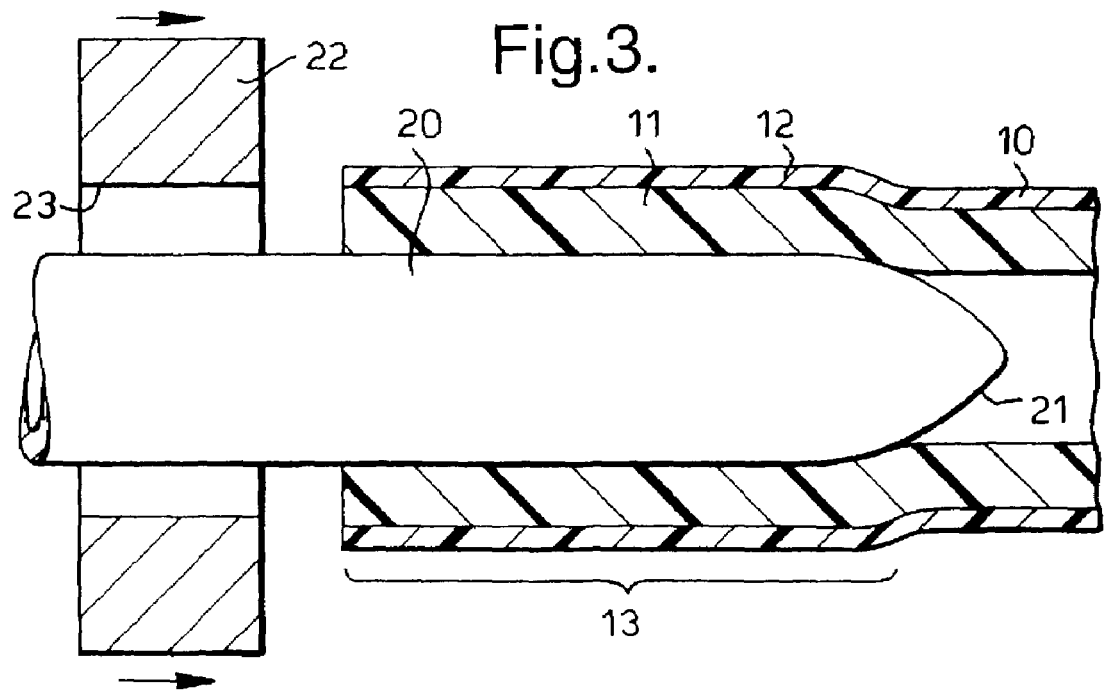

The next step, as shown in FIG. 3, is to insert a heated pin 20 into one end of the tubing 10. The pin 20 has pointed tip 21 and is of circular section, the diameter of the pin in its cylindrical section being approximately equal to the external diameter of the tubing 10 less the thickness of the inner layer 11. The heat of the pin 20 softens the material of the tubing 10 sufficiently to enable the tubing to be deformed outwardly over the surface of the pin, which may be lubricated to assist insertion. The pin 20 is inserted in the tubing 10 by a sufficient distance to produce an enlarged region 13 equal to the desired length of the soft region 5 of the catheter 1. While the pin 20 is still in place, an annular grinding tool 22 is rotated about the axis of the pin and is moved forwards along the length of the pin. The tool 22 has a central aperture 23 with a diameter equal to the external diameter of the unexpanded part of the tubing 10. As the tool 22 rotates and moves forwards, it grinds away the outer part of the enlarged region 13 of the tubing 10. More particularly, it removes the hard outer layer 12 of the tubing 10 along the expanded region 13 of tubing through the entire thickness of the outer layer, exposing the softer, inner layer 11 on the outside surface.

Figure 4:
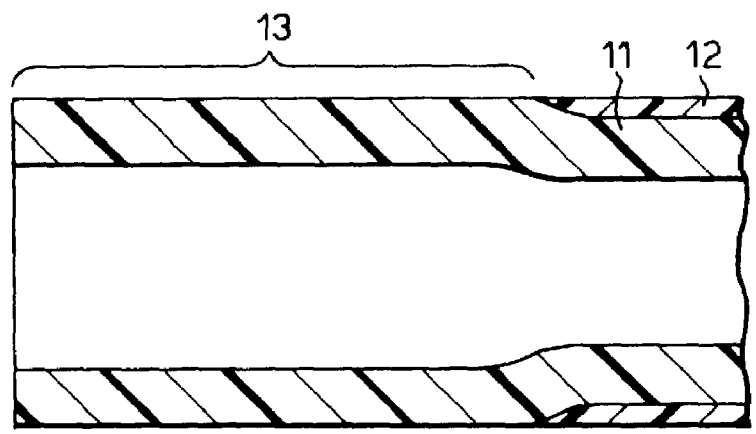

The grinding tool 22 is then slid back and the pin 20 is removed from the tubing 10, which now has the form shown in FIG. 4. The surface of the ground region may be smoothed to remove machining marks, such as by applying a solvent or thin coating, or by the application of heat. The tubing 10 has a constant external diameter along its length, with the hard outer layer 12 making the tubing relatively stiff along most of its length compared with the region 13 from which the hard layer has been removed and which is now solely provided by the relatively soft inner layer 11. The reduced overall wall thickness along the region 13 also contributes to the softer, more flexible nature of this region. The internal diameter of the tubing is slightly greater along the region 13 but, providing the hard outer layer 12 is relatively thin compared with the inner layer, this variation in internal diameter need not be great.

Figure 5:
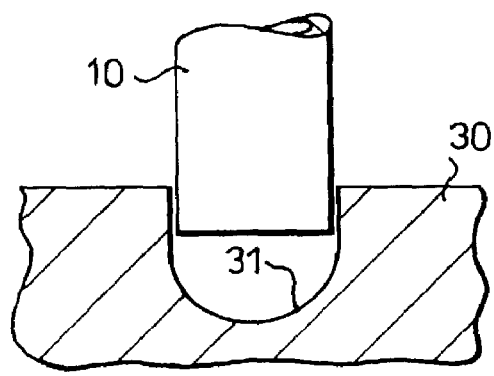
Figure 6:
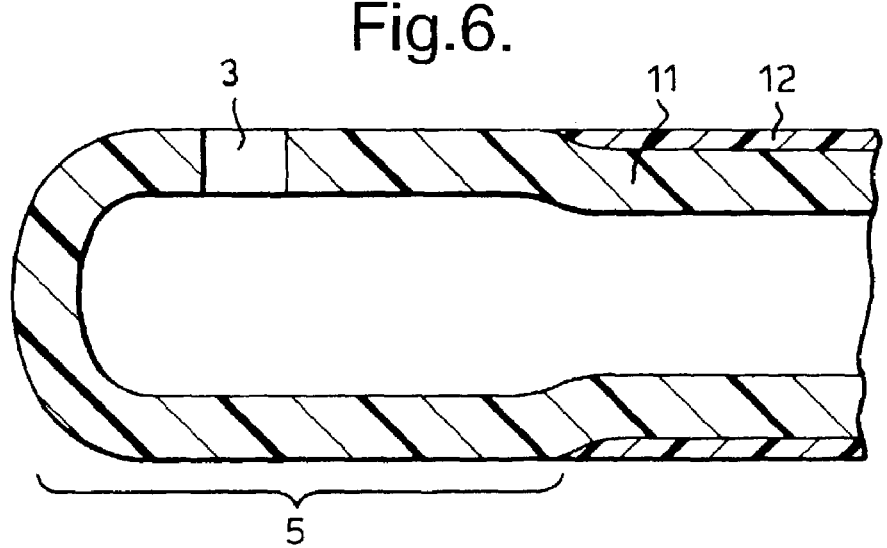
FIG. 6 is an enlarged cross-sectional side elevation view of the patient end of the finished catheter.

The next step, as shown in FIG. 5, is to end form the tubing 10 in a conventional way, by pushing it into a heated mould 30 having a cavity 31 shaped to close and define the shape of the end 2 of the catheter. The side eye 3 is then formed through the soft region 5 in a conventional way to produce a closed-tip, side-opening catheter, as shown in FIG. 6.

The soft nature of the very tip of the catheter, along the first 2-3 mm provides a soft bumper in case the tip collides with patient tissue during insertion. The more flexible nature of the remainder of the region 5 allows the catheter to take a route of low resistance, thereby avoiding collisions with hard parts of the anatomy. The construction of the catheter enables it to be made easily by automated processes and without the need for subsequent assembly operations.

It will be appreciated that the invention is not confined to epidural catheters but could be used to provide a region of increased softness and flexibility to other tubes such as endotracheal tubes. In some cases, the region of increased softness might not be the tip of the catheter. It may not be necessary in some tubes completely to remove the entire thickness of the outer layer in order to produce the desired softness. The catheter could be reinforced such as by incorporating a helical reinforcing element, or a braid into the outer layer. A lumen could be formed along either layer for various conventional purposes. There are various other ways in which the outer layer could be removed at the tip of the catheter instead of by mechanical grinding.

What I claim is:

1. A method of making a medico-surgical tube comprising the steps of: providing a tubular member with an inner layer and an outer layer, said outer layer being of a harder material than said inner layer; enlarging the internal diameter of said tubular member by inserting a heated pin in said tubular member along a region of said tubular member; and subsequently removing a part at least of said outer layer along said region to make said region softer and more flexible than the remainder of said tube.

2. A method according to claim 1, wherein the said part at least of said outer layer is removed along said region to a thickness such that the external diameter of said region is substantially equal to that of the remainder of said tube.

3. A method according to claim 1, wherein said outer layer is removed through its entire thickness along said region.

4. A method according to claim 1, wherein the diameter of said pin is substantially equal to the external diameter of said tubular member less the thickness of said inner layer.

5. A method according to claim 1, wherein the said part at least of said outer layer is removed by grinding while said heated pin is in said tubular member.

6. A method according to claim 1, wherein the said part at least of said outer layer is removed by moving an annular grinding tool axially along said region.

7. A method according to claim 1 including the step of smoothing said region after removing the said part at least of said outer layer.

8. A method according to claim 1, wherein said region is at one end of said tube.

9. A method according to claim 8, wherein said region is at a patient end of said tube.

10. A method according to claim 8 including the step of subsequently end forming the said end of said tube closed and forming a side opening in said tube in said region.

11. A method according to claim 1, wherein said tubular member is provided by extruding.

* * * * *